US 9,389,160 B2

(12) United States Patent
Ohl et al.

(10) Patent No.: US 9,389,160 B2
(45) Date of Patent: Jul. 12, 2016

(54) CAVITATION SENSOR

(75) Inventors: Claus-Dieter Ohl, Singapore (SG); Silvestre Roberto Gonzalez-Avila, Singapore (SG)

(73) Assignee: Nanyang Technological University, Singapore (SG)

( * ) Notice: Subject to any disclaimer, the term of this patent is extended or adjusted under 35 U.S.C. 154(b) by 499 days.

(21) Appl. No.: 13/878,536

(22) PCT Filed: Oct. 15, 2010

(86) PCT No.: PCT/SG2010/000397
§ 371 (c)(1),
(2), (4) Date: Jul. 24, 2013

(87) PCT Pub. No.: WO2012/050522
PCT Pub. Date: Apr. 19, 2012

(65) Prior Publication Data
US 2013/0298646 A1  Nov. 14, 2013

(51) Int. Cl.
*G01N 13/00* (2006.01)
*G01F 1/64* (2006.01)
*G01N 27/06* (2006.01)

(52) U.S. Cl.
CPC ............... *G01N 13/00* (2013.01); *G01N 27/06* (2013.01)

(58) Field of Classification Search
CPC .................................. G01N 13/00; G01F 1/64
USPC ................... 73/53.01, 60.11, 861.08–861.17
See application file for complete search history.

(56) References Cited

U.S. PATENT DOCUMENTS

| 4,254,377 A | * | 3/1981 | Findl | G01N 27/60 204/450 |
| 6,206,646 B1 | | 3/2001 | Bucher | |
| 6,450,184 B1 | | 9/2002 | Azar | |
| 6,497,140 B1 | * | 12/2002 | Zeqiri | G01H 11/08 73/19.03 |
| 7,057,973 B2 | * | 6/2006 | Ferrell | G01N 21/1702 367/131 |

(Continued)

FOREIGN PATENT DOCUMENTS

JP            06-300725            10/1994

OTHER PUBLICATIONS

Kim, W., et al., "Mechanism of particle removal by megasonic waves", Applied Physics Letters, vol. 94, pp. 081908-1-081908-3 (2009).

(Continued)

*Primary Examiner* — Hezron E Williams
*Assistant Examiner* — Hoang Nguyen
(74) *Attorney, Agent, or Firm* — Schiff Hardin LLP

(57) ABSTRACT

According to various embodiments, a cavitation sensor for detecting bubbles in a liquid is provided. The cavitation sensor may include: a substrate having an insulative surface; and an electrode arrangement provided on or within the insulative surface of the substrate. The electrode arrangement may include a first electrode and a second electrode being isolated from each other by the insulative surface, each of the first and the second electrode including a sensing portion. The spacing between the sensing portion of the first electrode and the sensing portion of the second electrode is adapted to allow charge flow between the first electrode and the second electrode caused by cavitation occurring at the sensing portion.

20 Claims, 9 Drawing Sheets

(56) References Cited

U.S. PATENT DOCUMENTS

| | | | |
|---|---|---|---|
| 7,111,517 B2* | 9/2006 | Kerr | B08B 3/00 134/113 |
| 7,210,354 B2* | 5/2007 | Puskas | B01J 19/10 73/590 |
| 2003/0115952 A1* | 6/2003 | Mayer | G01F 1/6845 73/204.26 |
| 2007/0113644 A1* | 5/2007 | Manaka | G01F 1/684 73/204.26 |

OTHER PUBLICATIONS

Krefting, D., et al., "High-speed observation of acoustic cavitation erosion in multibubble systems", Ultrasonics Sonochemistry, vol. 11, pp. 119-123 (2004).

Ohl, C.-D., et al., "Surface cleaning from laser-induced cavitation bubbles", Applied Physics Letters, vol. 89, pp. 074102-1-074102-3 (2006).

Zembala, M., "Electrokinetics of heterogeneous interfaces", Advances in Colloid and Interface Science, vol. 112, pp. 59-92 (2004).

Minnaert, M. "On Musical Air-Bubbles and the Sounds of Running Water", Philosophical Magazine, vol. 16, pp. 235-248 (1933).

Lauterborn, W., "Numerical investigation of nonlinear oscillations of gas bubbles in liquids", Journal of the Acoustical Society of America, vol. 59, No. 2, pp. 283-293 (Feb. 1976).

Jan. 6, 2011 International Search Report from PCT International Application No. PCT/SG2010/000397.

* cited by examiner

CAVITATION SENSOR

TECHNICAL FIELD

Various embodiments relate to a cavitation sensor for detecting bubbles in a liquid.

BACKGROUND

Cavitation is the occurrence of empty voids in liquids. Being a statistical phenomenon, its position, duration and strength is difficult to predict. Two classical areas of cavitation are hydrodynamic and acoustic cavitation.

Hydrodynamic cavitation occurs in regions with low suction pressure, e.g. in inducers of rocket engines and turbo machinery, and is typically unavoidable. For turbo machinery, a safe operating region has to be found as cavitation occurring close to a rigid boundary can lead to its erosion.

Acoustic cavitation refers to induced cavitation for the purpose of ultrasonic cleaning. An acoustic field induces small bubbles in a liquid to radial oscillations. When the bubbles oscillate at a boundary they create sufficient shear stress to remove contamination from the surface and transport the dirt particulate into the bulk flow.

There is interest, for example in the semiconductor industry, in a sensor that can measure the amount of cavitation activity on a surface to control and optimize cleaning of silicon wafers, while mitigating damaging of delicate structures fabricated in the silicon wafers. Several known cavitation sensors are discussed below.

U.S. Pat. No. 7,210,354 discloses a system having a conductivity sensor, photo sensor, and thermocouple (B2) to measure radical production, light emission and heat generated by cavitation. However, the disclosed system is unable to indicate if the bubbles are creating a flow on the surface to be cleaned.

U.S. Pat. No. 6,497,140 discloses a cavitation sensor based on the measurement of acoustic signatures from oscillating bubbles within an acoustic chamber. The cavitation sensor has a size in the centimeter range. Such a size may lead to gaseous bodies becoming entrapped, thereby disturbing an acoustic field generated or leading to additional cavitation nuclei. Further, as the disclosed sensor needs to be flushed with liquid, it can only measure the pressure in the bulk liquid and not close to a surface. Further, this sensor does not detect the flow created but only the acoustic signals emitted from the oscillating bubbles. Further, this signature is a complex superposition of the emission of many bubbles, thus it is a complex inverse problem to deduce from this signal any meaningful physical quantity bubbles may have on surfaces.

U.S. Pat. No. 7,057,973 discloses a sensor that measures light emitted from sonoluminescence of a sampling liquid in which bubbles collapse. A photomultiplier detects the light from the sampling liquid which is either flush with a light-tight sensor housing or contains a fixed amount of liquid in a closed volume. The detection of cavitation is thus in an indirect manner, so the sensor does not detect whether the bubbles are creating a flow on the surface to be cleaned. Due to the use of photomultipliers, the cost is high.

U.S. Pat. No. 6,450,184 discloses piezoelectric discs assembled on a substrate and connected to a read-out unit. Piezoelectric sensors are sensitive to force acting on their surface and experience displacement from, for example, bubbles oscillating on the surface. However, an acoustic wave or the force from a liquid accelerated by the bubble will also lead to a signal output from the sensors. Thus, it is difficult to determine whether a signal from the sensor is caused from bubble emitted sound at some distance from the surface or from a bubble oscillating on the surface. The latter is the main contributor to surface cleaning, although the size of the sensor provides for the probability that signal arises from the former. The sensor size also does not enable easy integration with the object under probe.

U.S. Pat. No. 7,111,517 discloses cavitation sensing in wafer cleaning tools. The cavitation sensors are pressure sensing elements on a substrate to measure the activity of bubbles on the substrate. Similar to the piezoelectric sensors of U.S. Pat. No. 6,450,184, the pressures sensing elements experience displacement when force is applied to them. Thus, the focus is on the measurement of pressures, rather than flow strength.

There is thus a need to provide a cavitation sensor that detects cavitation occurring close to the sensor surface and is unaffected by cavitation that occurs at another portion of the liquid that the cavitation sensor is placed in.

SUMMARY

Disclosed herein is a cavitation sensor. The cavitation sensor may include: a substrate having an insulative surface; and an electrode arrangement provided on or within the insulative surface of the substrate. The electrode arrangement may include a first electrode and a second electrode being isolated from each other by the insulative surface, each of the first and the second electrode including a sensing portion. The spacing between the sensing portion of the first electrode and the sensing portion of the second electrode is adapted to allow charge flow between the first electrode and the second electrode caused by cavitation occurring at the sensing portion.

The cavitation sensor may be a device suitable for the purpose of detecting any kind of bubbles, caused by cavitation, in a liquid. Cavitation bubbles may be induced through agitating a solution with a laser, thereby creating regular reproducible bubbles. Another way of creating cavitation bubbles is through the use of an ultrasonic transducer, although such bubbles are created in a more random manner than those created through laser agitation. The acoustic field brings small bubbles in a liquid to radial oscillations.

When the bubbles oscillate at a boundary they create sufficient shear stress to remove contamination from the surface and transport dirt particulate into bulk flow. Thus, a cavitation sensor may find applications in, for example, the semiconductor industry, where cavitation is induced to clean silicon wafers. A cavitation sensor described herein may provide a sensor which can measure the amount of cavitation activity on the surface of silicon wafers to control and optimize the cleaning process of silicon wafers while mitigating damaging of delicate structures which may be fabricated on them. Other industrial processes that use cavitation and would benefit from a sensor according to various embodiments include waste and fresh water treatment, dying of textiles and leather, cleaning of membranes, ultrasound emulsification and cell disrupter, and the whole field of sonochemistry.

In a cavitation sensor described herein, the term "substrate" may be understood as a base material upon which the electrode arrangement is fabricated. The substrate has an insulative surface or may be entirely made of insulative material. In a cavitation sensor described herein, the term "insulative" may be understood as isolating electricity flow within electrical conductors formed on or within the substrate, thereby preventing a short circuit between physically unconnected electrical conductors.

In a cavitation sensor described herein, the term "electrode arrangement" means a plurality of electrodes, each of which having a sensing portion that is exposed and thereby in contact with the liquid where cavitation bubbles are to be detected. Electrodes may be fabricated from any electrical conducting material and having any shape (for example, strips) depending on the size of the bubbles that are to be detected. The electrodes may have a regular or irregular cross-section, so that the width of the electrodes may vary as they span over the substrate.

In a cavitation sensor described herein, the term "spacing" means an electrical insulating portion between the sensing portion of the first electrode and the sensing portion of the second electrode. The electrical insulating portion may be realised by a portion of the substrate between the sensing portion of the first electrode and the sensing portion of the second electrode or a gap created by cutting away the substrate between the sensing portion of the first electrode and the sensing portion of the second electrode.

In a cavitation sensor described herein, the term "charge flow" refers to the current flow due to charges close to the surface, being a function of the velocity of liquid at the sensing portion of the first electrode and the sensing portion of the second electrode. Without being bound by theory, the velocity of the liquid drops to zero at the substrate surface, whereby an electric current is generated a small distance from the substrate surface. The current will be a function of velocity gradient, i.e. the wall normal gradient of the velocity parallel to the wall. This quantity is related to the physical quantity called wall shear stress.

In a cavitation sensor described herein, the sensing portion of the first electrode and the sensing portion of the second electrode are configured to remain stationary relative to the substrate and is sensitive to the wall shear stress caused by the change of the velocity component parallel to the wall. In other words, the sensing portion of the first electrode and the sensing portion of the second electrode may be configured to remain stationary relative to the substrate, to detect a change in the velocity of liquid flowing parallel to the substrate surface where the electrode arrangement is provided on.

In a cavitation sensor described herein, the electrode arrangement may be a layer with a thickness that allows sufficient cohesion to the substrate surface, such as around 300 nm.

In a cavitation sensor described herein, the sensing portion of the first electrode and the sensing portion of the second electrode may include a strip.

In a cavitation sensor described herein, the strip of the first electrode may have an end which is disc shaped, while the strip of the second electrode may have an end that partially surrounds the disc shaped end of the first electrode to form a crook shape.

In a cavitation sensor described herein, the disc shaped end may have a radius of around 0.2 mm and the crook shape may have an inner radius of around 0.25 mm.

In a cavitation sensor described herein, the strip of the first electrode and the strip of the second electrode may each have a width of around 0.1 mm. The strip of the first electrode, in one example, may not be parallel to the strip of the second electrode. For instance, a tapered portion may be formed by the spacing between the strip of the first electrode and the strip of the second electrode tapering towards the corresponding end of the first electrode and the second electrode. The spacing between the strip of the first electrode and the strip of the second electrode may range from about 0.001 mm (1 um) to about 0.3 mm (300 um). It is also possible that the spacing may be from about 0.05 mm to about 0.3 mm.

The strip of the first electrode may be parallel to the strip of the second electrode. The strip of the first electrode and the strip of the second electrode may be spaced around 0.05 mm apart. The 0.05 mm spacing may be uniform where the strip of the first electrode is parallel to the strip of the second electrode. The ratio of the space between the strip of the first electrode and the strip of the second electrode; and the width of the strip of the first electrode and the strip of the second electrode may have any one of the values of 1, 1.5, 1.75 and 2.

In a cavitation sensor described herein, the electrode arrangement may include one or more arrays, each array including one or more pairs of first electrodes and second electrodes.

Each array may include a first common terminal to which each of the first electrodes of the one or more pairs are coupled; and a second common terminal to which each of the second electrodes of the one or more pairs are coupled.

In a cavitation sensor described herein, the pairs of electrodes may be arranged such that first electrodes and second electrodes alternate with each other. In a cavitation sensor described herein, the term "alternate" may mean that when considering any two electrodes, the first electrode is disposed immediately adjacent to the second electrode.

In a cavitation sensor described herein, the first common terminal and the second common terminal may be arranged parallel to each other, wherein the first and second electrodes may be arranged parallel to each other, and wherein the first and second electrodes are arranged perpendicular to the first common terminal and the second common terminal.

The first common terminals of a first array of the one or more arrays and a second array of the one or more arrays may be coupled together, or wherein the second common terminals of the first array and the second array may be coupled together. However, it is also possible that each of the first common terminals may not be coupled together and each of the second common terminals may not be coupled together, so that cavitation occurring at any of the one or more arrays may be measured separately.

The distance between adjacent electrodes for one of the one or more arrays may be different from the distance between adjacent electrodes for another of the one or more arrays. However, it is also possible that the distance between adjacent electrodes in all of the one or more arrays may be the same.

In a cavitation sensor described herein, the maximum distance between adjacent electrodes for the one or more arrays may be about less than half of the diameter of the bubble to be detected.

In a cavitation sensor described herein, the spacing between the sensing portion of the first electrode and the sensing portion of the second electrode may be smaller than a diameter of a bubble to be detected. However, it is also possible that the maximum spacing between the sensing portion of the first electrode and the sensing portion of the second electrode may be about less than half of the diameter of the bubble to be detected.

In a cavitation sensor described herein, the sensing portion of the first electrode and the sensing portion of the second electrode may be provided on a common plane.

In a cavitation sensor described herein, the substrate may include glass.

In a cavitation sensor described herein, the electrode arrangement may include any conducting material. The conducting material may include any one or more of gold, platinum, indium tin oxide and titanium. The sensing portion of the electrode arrangement may be provided on the insulative surface of the substrate, while at least a portion of the remainder of the electrode arrangement may be provided within the insulative surface of the substrate. The cavitation sensor may further include a further insulative layer, wherein the sensing portion of the electrode arrangement is provided on the insulative surface of the substrate, while the further insulative layer is provided on at least a portion of the remainder of the electrode arrangement. The further insulative material may be of the same material as the substrate.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DETAILED DESCRIPTION

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

Disclosed herein is a cavitation sensor sensitive to shear flow, i.e. flow which is able to transport charges in the Debye layer close to the sensor surface. The flow sensing may be, for instance, from the surface to around 100 nm from the surface. Large scale flows or bubbles far from the boundary may not be detected, only flow created by a cavitation bubble in close proximity to the sensing portion of the cavitation sensor. The cavitation sensor is compact, sturdy and durable, having two thin metallic electrodes isolated from each other, e.g. two gold patches with glass in between. Since only a thin layer of metal such as gold needs to be deposited onto a substrate, a cavitation sensor as described herein is simple to manufacture. Being inexpensive, the cavitation sensor is disposable after usage. The cavitation sensor may be integrated into the surface exposed to cavitation, thereby providing a sensor that can measure the direction of liquid flow.

The cavitation sensor disclosed herein may have two conductive and thin patches of variable shape termed electrodes. They are deposited onto an isolator or semiconductor. The height of the patch is thin, typically less than one micrometer. The isolator between the two electrodes may be; or comprise, glass, silicon, or any material with sufficient strength. The electrodes may be made of gold, platinum, or another conducting material. The patches are connected to a conductor to transport the signal to read-out electronics via a connector patch. The design of the distance between the sensor-electrodes may be guided by the size of the bubble to be measured. The distance is approximately $\frac{1}{20}^{th}$ to $\frac{1}{5}^{th}$ of typical bubble diameter. The conductors may be isolated with a passivating layer (isolator) to prevent leak current between the conductors.

The shape of the electrodes may be designed according to the type of cavitation of interest and thus may vary.

Figure 1:
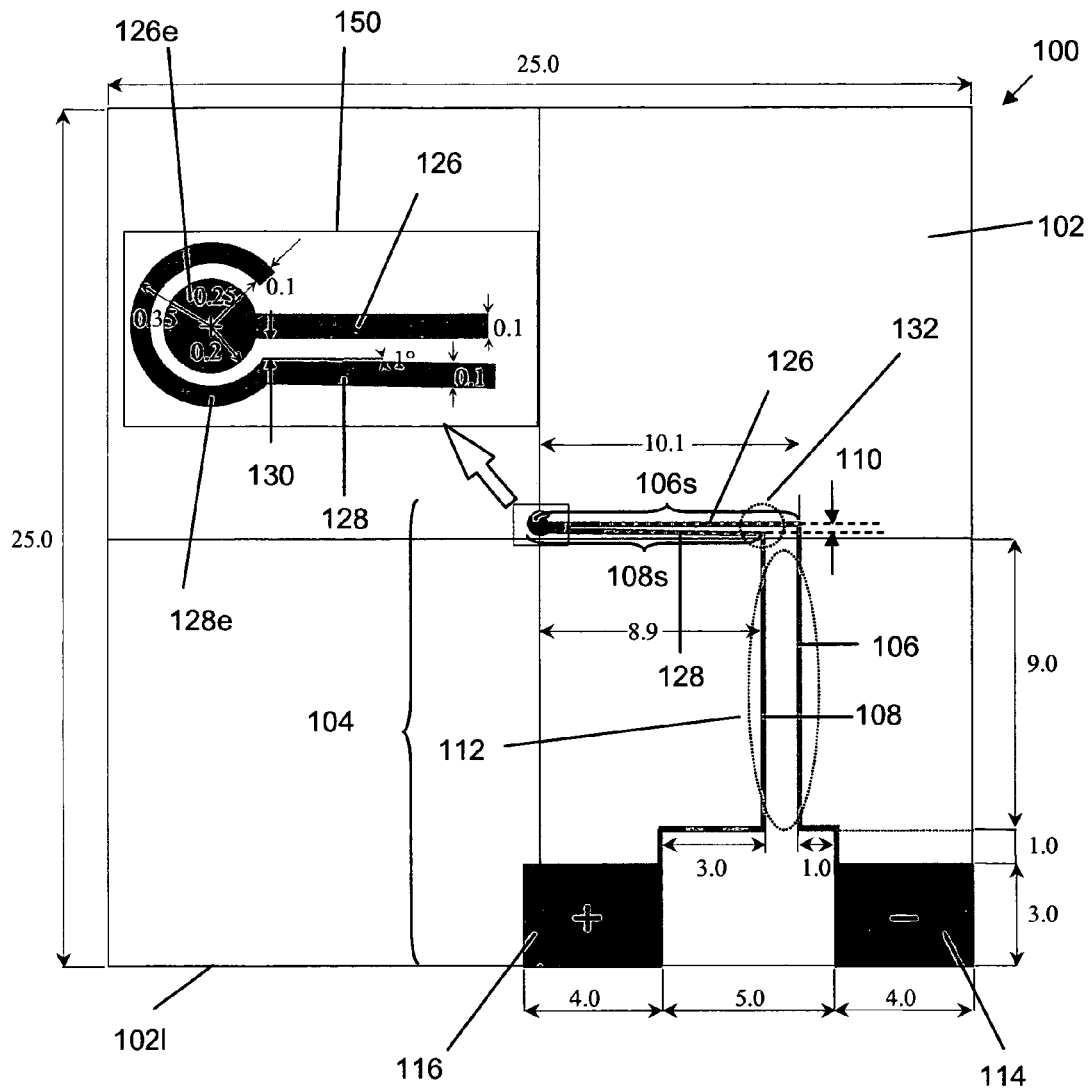
FIG. 1 is a top view of one embodiment of a cavitation sensor.

FIG. 1 is a top view of one embodiment of a cavitation sensor 100. The cavitation sensor 100 is suitable for detecting bubbles in a liquid.

The cavitation sensor 100 has a substrate 102 having an insulative surface; and an electrode arrangement 104, which is shown in the embodiment of FIG. 1 to be provided on the insulative surface of the substrate 102. In another embodiment (not shown), the electrode arrangement may be provided within the insulative surface of the substrate.

The electrode arrangement 104 includes a first electrode 106 and a second electrode 108 being isolated from each other by the insulative surface. Each of the first and the second electrode (106, 108) includes a sensing portion (106s for the first electrode 106 and 108s for the second electrode 108). The spacing 110 between the sensing portion 106s of the first electrode 106 and the sensing portion 108s of the second electrode 108 is adapted to allow charge flow between the first electrode 106 and the second electrode 108 caused by cavitation occurring at the sensing portion.

Charge flow between the sensing portion 106s of the first electrode 106 and the sensing portion 108s of the second electrode 108 occurs due to the existence of an electrical double layer (EDL) on the surface of the substrate 102. The EDL refers to two parallel layers of charge on the surface of the substrate 102. The first layer, the surface charge (either positive or negative), comprises ions adsorbed directly onto the object due to chemical interactions. The second layer is composed of ions attracted to the surface charge via Coulomb force, electrically screening the first layer. The second layer is loosely associated with the surface of the substrate 102, as the second layer is made of free ions which move in the liquid under the influence of electric attraction and thermal motion rather than being firmly anchored, thereby forming a diffuse layer. At least a part of the diffuse layer can move under the influence of tangential stress. Such stress can arise from, for example, impact of cavitation bubbles on the surface of the substrate 102. Thus when a bubble impacts in the vicinity of or on the sensing portions 106s and 108s, current flow occurs between the sensing portion 106s of the first electrode 106 and the sensing portion 108s due to the displacement of charges in the second layer. Accordingly, should there be bubbles of sufficient size, charge flow can also occur at portion 112 of the first electrode 106 and the second electrode 108. A more detailed discussion on the existence of the EDL can be found, for instance, in the publication "Electrokinetics of heterogeneous interfaces" by Maria Zembala from *Advances in Colloid and Interface Science* 112 (2004) 59-92.

The sensing portion 106s of the first electrode 106 has a longer length than the sensing portion 108s of the second electrode 108, so that the spacing 110 between the sensing portions (106s and 108s) is smaller than the spacing between the first electrode 106 and the second electrode 108 at the portion 112. It will be appreciated that the length of the sensing portion 106s and the length of the sensing portion 108s may be arbitrarily chosen, where in exemplary embodiments, suitable lengths are around 10.1 mm and around 8.9 mm respectively. Lengths shorter than 10.1 mm and 8.9 mm are also possible, where shorter lengths provide the additional advantage of reducing electromagnetic pickup, as long as the sensing ends 126e and 128e are connectible to terminals (114, 116) which are for connection to amplifiers (not shown).

In the embodiment shown in FIG. 1, the first electrode 106 includes a first terminal 114, while the second electrode 108 includes a second terminal 116. The first terminal 114 and the second terminal 116 are positioned to be along an edge 102l of the substrate 102. The terminals 114 and 116 provide for signals from the cavitation sensor 100 to be tapped and amplified, where the amplified signals may then be analysed in an oscilloscope. Each of the terminals 114 and 116 has a dimension of around 3 mm by 4 mm, where they are spaced a distance of around 5 mm along the edge 102l. In the embodiment shown in FIG. 1, the substrate has a square shape of dimensions 25 mm by 25 mm.

Being formed on the surface of the substrate 102, the sensing portion 106s of the first electrode 106 and the sensing portion 108s of the second electrode 108 are configured to remain stationary relative to the substrate 102. The sensing portions 106s and 108s remain stationary, relative to the substrate 102, to shear stress applied on the electrode sensing portions (106s and 108s) from a change in the velocity of liquid at the sensing portion 106s of the first electrode 106 and the sensing portion 108s of the second electrode 108, caused by cavitation. This is in contradistinction to piezoelectric or pressure sensors, which experience displacement when pressure is applied on them.

The electrode arrangement 104 may have any suitable thickness, such as around 300 nm. The electrode arrangement 104, may for example, be formed from coating or depositing on the substrate 102 surface a layer of electrode material (such as gold) and then performing a selective etch to remove undesired portions.

The sensing portion 106s of the first electrode 106 and the sensing portion 108s of the second electrode 108 may include a strip (126 and 128 respectively). Referring to the inset 150, the strip 126 of the first electrode 106 may have an end 126e which is disc shaped, while the strip 128 of the second electrode 108 may have an end 128e that partially surrounds the disc shaped end 126e of the first electrode 108 to form a crook shape.

The disc shaped end 126e may have a radius of around 0.2 mm and the crook shape may have an inner radius of around 0.25 mm. The strip 126 of the first electrode 106 and the strip 128 of the second electrode 108 may each have a width of around 0.1 mm.

In the embodiment shown in FIG. 1, a regular gap of around 0.05 mm exists between the disc shaped end 126e and the crook shaped end 128e. However, the strip 126 of the first electrode 106 is not parallel to the strip 128 of the second electrode 108. The spacing 110 between the strip 126 of the first electrode 106 and the strip 128 of the second electrode 108 tapers towards the corresponding end (i.e. 126e and 128e) of the first electrode 106 and the second electrode 108, the tapering ensuring that detection occurs mainly at the disc shaped end 126e and the crook shaped end 128e.

The tapering spacing between the strip 126 of the first electrode 106 and the strip 128 of the second electrode 108 is such that there is a smallest spacing 130 of about 0.001 mm and a largest spacing 132 of about 0.3 mm. It is also possible that, where a regular gap of around 0.05 mm exists between the disc shaped end 126e and the crook shaped end 128e, the smallest spacing 130 is about 0.05 mm and a largest spacing 132 of about 0.3 mm. In the embodiment shown in FIG. 1, the tapering is created by having the strip 128 incline about 1° to an axis parallel to the edge 102l, so that the disc shaped end 126e and the crook shaped end 128e detect cavitation bubbles of maximum diameter of approximately 1 mm. In other embodiments (not shown), the tapering may be created either by inclining the other strip or both strips.

The electrode arrangement 104 may also be designed such that detection occurs mainly at the disc shaped end 126e and the crook shaped end 128e. In such embodiments, the strip 126 and the strip 128 are not sensitive to flow and act as connecting strips to amplifiers (not shown) through the first terminal 114 and the second terminal 116 respectively. This may be achieved in several ways. For instance, the smallest spacing 130 between the first electrode 106 and the second electrode 108 may be spaced a distance of more than 300 um. Alternatively, only the sensing portion of the electrode arrangement 104 (i.e. the disc shaped end 126e and the crook shaped end 128e for the embodiment shown in FIG. 1) may be provided on the insulative surface of the substrate, while at least a portion of the remainder of the electrode arrangement is provided within the insulative surface of the substrate. As a further possibility, the cavitation sensor may include a further insulative layer, wherein the sensing portion (i.e. the disc shaped end 126e and the crook shaped end 128e for the embodiment shown in FIG. 1) of the electrode arrangement is provided on the insulative surface of the substrate, while the further insulative layer is provided on at least a portion of the remainder of the electrode arrangement. The further insulative material may be of the same material as the substrate.

In the embodiment shown in FIG. 1, the disc shaped end 126e and the crook shaped end 128e are positioned around the centre of the substrate 102. However, it will be appreciated that in other embodiments (not shown), the disc shaped end and the crook shaped end may be positioned on any portion of the substrate 102 surface.

The spacing 110 between the sensing portion 106s of the first electrode 106 and the sensing portion 108s of the second electrode 108 is smaller than a diameter of a bubble to be detected. The spacing 110 between the sensing portion 106s of the first electrode 106 and the sensing portion 108s of the second electrode 108 is preferably of a maximum value being about less than half of the diameter of the bubble to be detected.

The sensing portion 106s of the first electrode 106 and the sensing portion 108s of the second electrode 108 are provided on a common plane. In the embodiment shown in FIG. 1, the common plane is parallel to the surface of the substrate 102.

FIGS. 2A to 2D show cross-sectional views (along with respective top views) of cavitation occurring on the surface of an electrode arrangement 250 immersed into a liquid. The electrode arrangement 250 is fabricated on a surface of a substrate 202, so as to provide a cavitation sensor.

The electrode arrangement 202 is similar to the one shown in the inset 150 of FIG. 1, so its structural features will not be further elaborated.

Figures 2A, 2B, 2C, 2D:
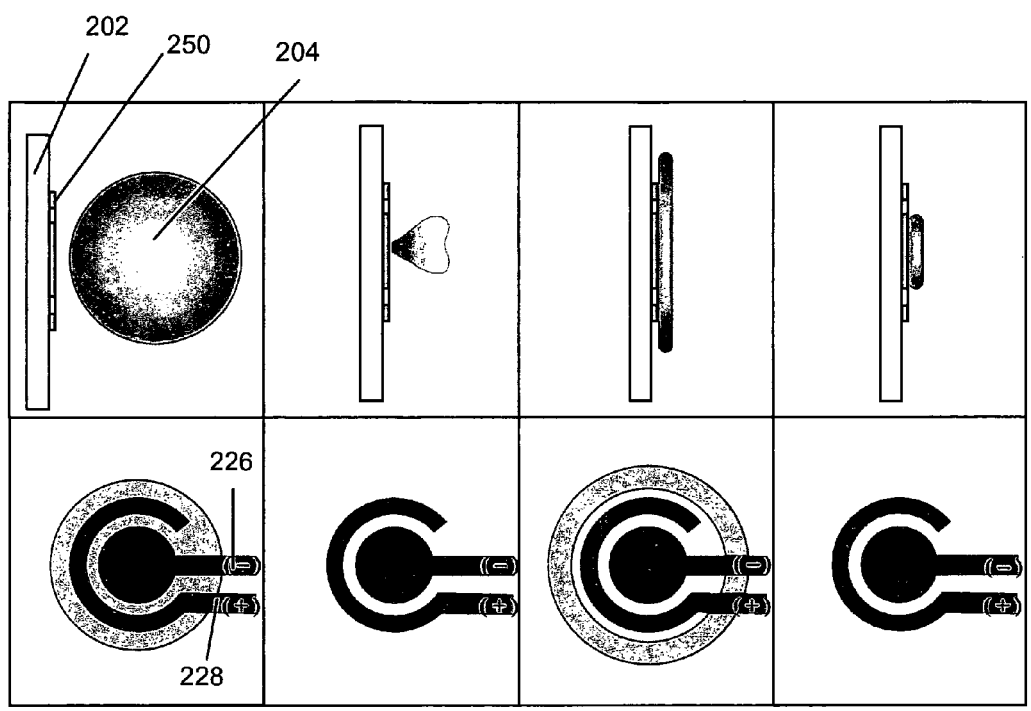
FIGS. 2A to 2D show cross-sectional views (along with respective top views) of cavitation occurring on the surface of an electrode arrangement of a cavitation sensor as described herein immersed into a liquid.

FIG. 2A shows a bubble 204 approaching the electrode arrangement 250. In FIG. 2B, the bubble 204 expands/collapses onto the surface of the electrode arrangement 250 and creates a fast liquid flow. During expansion, there will be a radial outward flow and during collapse, an inward flow which is superimposed with a jetting flow eventually spreads outwards on the surface as shown in FIG. 2C. A stably oscillating bubble leads to a repeating flow pattern. A transient bubble (vapor bubble) however, only oscillates few cycles until it condenses back into the liquid. If the flow pattern created by the bubble 204 is sufficiently strong it can modify the charge configuration in the Debye layer (as described in U.S. Pat. No. 4,254,377) on the electrode arrangement 250 and on the isolating substrate 202. A current of the amount $$I_s(t) = \int u(x,y,z,t)\rho(x,y,z,t)dzdA$$

is created, where u is the velocity component parallel to the sensor, $\rho$ the charge density distribution varying as a function of the distance from the surface z, and $dA=dxdy$ is the surface element on the electrode arrangement 250/substrate 202. The second electrode 228 collects this current which is returned back to the first electrode 226 through a current amplifier and return circuit (not shown). As the liquid flow is fast and the created current is small, the current amplifier needs to have sufficient bandwidth and sensitivity. To reduce the sensitivity of the electrode arrangement 250 to electromagnetic noise, the electrode arrangement 250 is connected to a resistor (not shown) of low impedance, with a suitable value of that of the input impedance of the current amplifier. For instance, a variable gain high-speed current amplifier such as DHPCA-100 from FEMTO Messtechnik GmbH, Berlin, Germany may be used.

Figure 3:
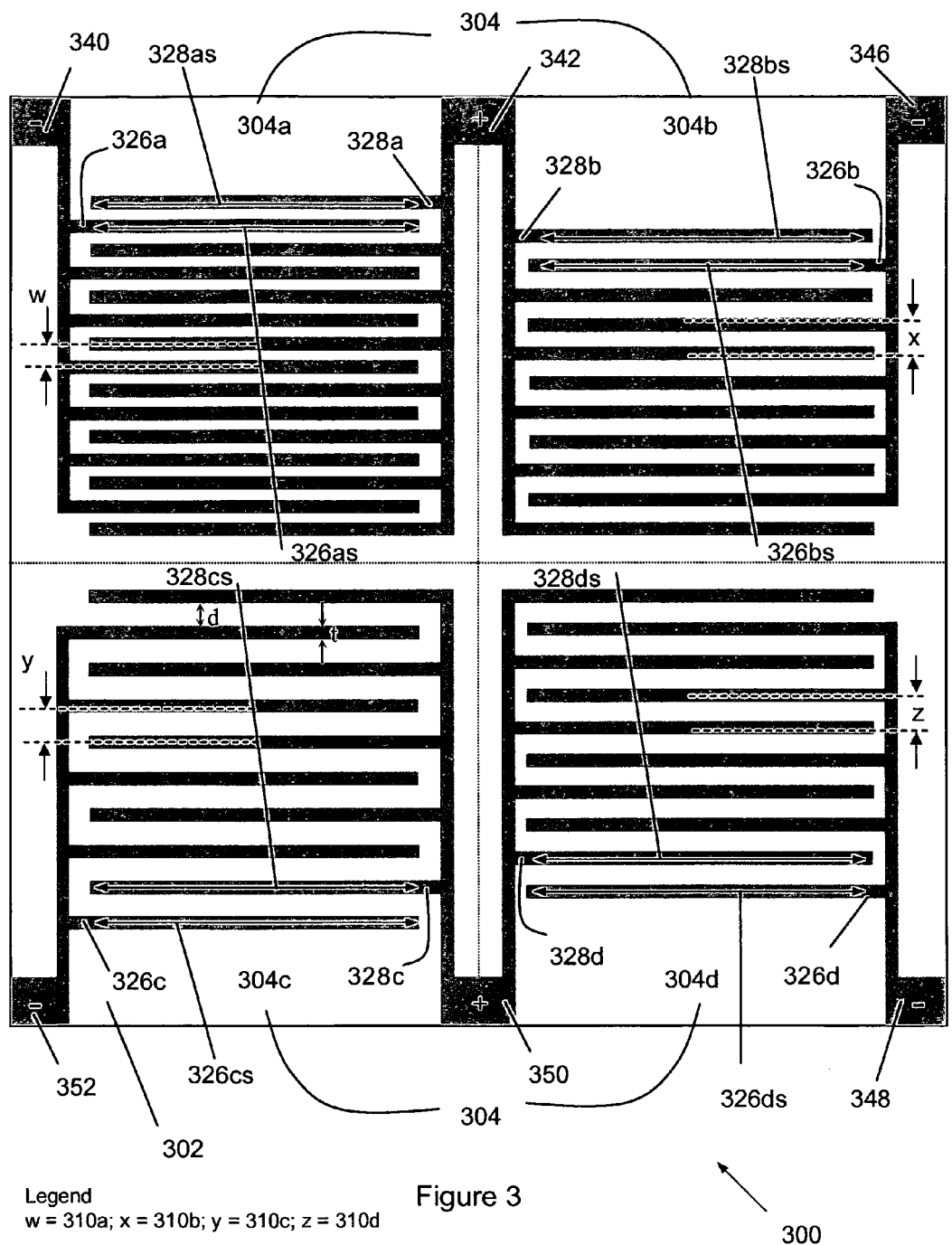
FIG. 3 is a top view of another embodiment of a cavitation sensor.

FIG. 3 is a top view of another embodiment of a cavitation sensor 300. The cavitation sensor 300 is suitable for detecting bubbles in a liquid.

Similar to FIG. 1, the cavitation sensor 300 has a substrate 302 having an insulative surface; and an electrode arrangement 304, which is shown in the embodiment of FIG. 3 to be provided on the insulative surface of the substrate 302. In another embodiment (not shown), the electrode arrangement may be provided within the insulative surface of the substrate.

The electrode arrangement 304 has one or more arrays (304a, 304b, 304c and 304d), each array including one or more pairs of first electrodes (326a, 326b, 326c and 326d) and second electrodes (328a, 328b, 328c and 328d). The pairs of electrodes may be arranged such that the first electrodes (326a, 326b, 326c and 326d) and the second electrodes (328a, 328b, 328c and 328d) alternate with each other, i.e. the first electrode (326a, 326b, 326c and 326d) is disposed immediately adjacent to the second electrode (328a, 328b, 328c and 328d). The embodiment shown in FIG. 3 illustrates an array of parallel wires or strips, but it is also possible to use (not shown) an array of concentric rings. It will be appreciated that the position of the electrode arrangement 304 can be varied to optimize the space on the surface of the substrate 302.

Each of the first electrodes (326a, 326b, 326c and 326d) and the second electrodes (328a, 328b, 328c and 328d) are isolated from each other by the insulative surface. Each of the first electrode and the second electrode (326a-d, 328a-d) includes a sensing portion (326as, 326bs, 326cs and 326ds; 328as, 328bs, 328cs and 328ds) which, in the embodiment shown in FIG. 3, extends across the lengths of the first and the second electrode (326a-d, 328a-d) that are adjacent to each other. The spacing (310a, 310b, 310c and 310d) between adjacent sensing portions (326as-ds) and (328as-ds) is adapted to allow charge flow between the respective first electrode (326a-d) and the second electrode (328a-d) caused by cavitation occurring at the sensing portion. The sensing portions (326as-ds) of the first electrodes (326a-d) and the sensing portions (328as-ds) of the second electrodes (328a-d) may be provided on a common plane. In the embodiment shown in FIG. 3, the common plane is parallel to the surface of the substrate 302.

Being formed on the surface of the substrate 302, the sensing portions (326as, 326bs, 326cs and 326ds; 328as, 328bs, 328cs and 328ds) are configured to remain stationary relative to the substrate 302. The sensing portions (326as, 326bs, 326cs and 326ds; 328as, 328bs, 328cs and 328ds) remain stationary, relative to the substrate 302, to applied shear stress from a change in the velocity of liquid at the sensing portions (326as, 326bs, 326cs and 326ds; 328as, 328bs, 328cs and 328ds) caused by cavitation. This is in contradistinction to piezoelectric or pressure sensors, which experience displacement when pressure is applied on them.

In the embodiment shown in FIG. 3, the sensing portion (326as-ds) of the first electrode (326a-d) and the sensing portion (328as-ds) of the second electrode (328a-d) are strips. The strip of the first electrode (326a-d) is parallel to the strip of the second electrode (328a-d) for all of the arrays (304a, 304b, 304c and 304d). Although the strips are parallel, the distance between adjacent electrodes (for example, 326a and 328a) for one (for, example 304a) of the one or more arrays is different from the distance between adjacent electrodes (for example, 326b and 328b) for another (for example 304b) of the one or more arrays, i.e. $310a \neq 310b \neq 310c \neq 310d$. However, within the same array (for example 304a), the distance between adjacent electrodes (for example 326a and 328a) is the same. In this manner, each array (304a, 304b, 304c and 304d) detects bubbles of a specific diameter, enabling the cavitation sensor 300 to detect bubbles of different diameter sizes. For the first array 304a, the strip of the first electrode 326a and the strip of the second electrode 328a may be spaced 310a around 0.05 mm apart. For the second array 304b, the strip of the first electrode 326b and the strip of the second electrode 328b may be spaced 310b around 0.07 mm apart. For the third array 304c, the strip of the first electrode 326c and the strip of the second electrode 328c may be spaced 310c around 0.09 mm apart. For the fourth array 304d, the strip of the first electrode 326d and the strip of the second electrode 328d may be spaced 310d around 0.1 mm apart. Since the strips are parallel, the spacing 310a-d is uniform within each respective array.

In other embodiments (not shown), the first electrode and the second electrode of any one or more arrays may not be parallel so that either tapers towards the other. The distance between adjacent electrodes in all of the one or more arrays may be the same for the case where the electrodes are parallel or not parallel.

Returning to the embodiment shown in FIG. 3, the ratio of the space (310a, 310b, 310c and 310d) between the strip of the first electrode (326a-d) and the strip of the second electrode (328a-d); and the width of the strip of the first electrode (326a-d) and the strip of the second electrode (328a-d) has the values of 1, 1.5, 1.75 and 2 respectively. It will be appreciated that these ratio values may be changed, depending on the size of the bubbles that are to be detected.

The optimum distance between adjacent electrodes in any one of the arrays (304a, 304b, 304c and 304d) is governed by the bubble size and the determination of bubble size is within the person of average skill in the art.

For example, it is known that cavitation bubbles create strong shear stress over an area of approximately $A = \pi R_{max}^2$ where $R_{max}$ is the maximum bubble radius. Accordingly, the spacing of the electrodes may be of about 0.1 to 0.5 times the maximum bubble radius. The linear resonance frequency of bubbles in water at room temperature is $$D*F=6 \text{ [m/s]},$$

where D is the resonant bubble diameter (measured in meters) and F the driving frequency (measured in Hertz [1/s]) may serve as a suitable design guide where the resonance diameter, D, is identified as the maximum bubble diameter, $R_{max}$. For a 20 kHz ultrasonic cleaning bath, the resonance diameter is approximately 0.300 mm, for 100 kHz the resonance diameter is 0.060 mm_and for 1 MHz the resonance diameter is about 6 microns. Thus for a 20 kHz ultrasonic cleaning bath, the gap between adjacent electrodes should be between 30 and 150 microns. For distances larger than about D a signal is not expected, as the flow dies out rapidly. More details on the relationship between bubble radius and resonance frequency may, for example, be found from the publication "On Musical Air-Bubbles and the Sounds of Running Water" by M. Minnaert, 1933, from *Philosophical Magazine*, vol. 16, pp 235-248.

Under strong driving as frequently observed in ultrasound cleaning applications the maximum bubble diameter (which is then a function of the pressure) can be determined by, for example, solving the non-linear bubble oscillation model or from measurements. More details can be found in the publication "Numerical investigation of nonlinear oscillations of gas bubbles in liquids" by Werner Lauterborn from *Journal of the Acoustical Society of America* Vol. 59, No. 2, February 1976 283-293.

Returning to the geometry of the electrode arrangement 304, the maximum distance between adjacent electrodes for the one or more arrays (304a, 304b, 304c and 304d) is preferably about less than half of the diameter of the bubble to be detected. Accordingly, the spacing (310a, 310b, 310c and 310d) between the sensing portion (326as-ds) and the sensing portion (328as-ds) is preferably smaller than a diameter of a bubble to be detected. Thus, different bubble sizes may be distinguished by using electrode geometries with different spacing.

Each of the arrays (304a, 304b, 304c and 304d) includes a first common terminal (340, 346, 348, 352) to which each of the first electrodes (326a, 326b, 326d, 326c) of one or more electrode pairs (326a, 328a; 326b, 328b; 326d, 328d; 326c, 328c) are coupled; and a second common terminal (342; 350) to which each of the second electrodes (328a, 328b; 328c, 328d) of the one or more electrode pairs (326a, 328a; 326b, 328b; 326d, 328d; 326c, 328c) are coupled.

The first common terminal (340, 346, 348, 352) and the second common terminal (342; 350) are arranged parallel to each other, while the first and second electrodes (326a, 328a; 326b, 328b; 326d, 328d; 326c, 328c) are arranged parallel to each other, while the first and second electrodes (326a, 328a; 326b, 328b; 326d, 328d; 326c, 328c) are arranged perpendicular to the first common terminal (340, 346, 348, 352) and the second common terminal (342; 350).

As shown in FIG. 3, the second common terminals 342 of the first array 304a and the second array 304b may be coupled together. The terminals 340 and 342 may then be connected to a first current amplifier, the terminals 342 and 346 may then be connected to a second current amplifier, the terminals 352 and 350 may then be connected to a third current amplifier and the terminals 350 and 348 may then be connected to a fourth current amplifier. A respective one of the four current amplifiers will have an output when cavitation bubbles impact electrodes of a corresponding one of the arrays (304a, 304b, 304c and 304d). In this manner, cavitation occurring at any of the one or more arrays (304a, 304b, 304c and 304d) may be measured separately.

Although not shown, the first common terminal 340 of a first array 304a of the one or more arrays (304a, 304b, 304c and 304d) and a first common terminal 346 of a second array 304b of the one or more arrays (304a, 304b, 304c and 304d) may be coupled together. Similarly, in other embodiments (not shown), each of the first common terminals may not be coupled together and each of the second common terminals may not be coupled together.

Referring to FIGS. 1 and 3, the substrate (102, 302) may be fabricated from glass. The electrode arrangement (104, 304) may be fabricated using any conducting material, such as any one or more of gold, platinum and titanium.

INDUSTRIAL APPLICATIONS

The cavitation sensor described herein provides for a sturdy and inexpensive sensor which is able to measure occurrence and strength of cavitation bubble induced flow on surfaces.

Hydrodynamic cavitation occurs in turbomachinery, ship propellers, ship rudders, high-speed pumps and pipelines. Thus, the cavitation sensor described herein may be used in all these environments to optimize operation parameters without structural damage.

Ultrasonic/megasonic cleaning is used in the semiconductor industry to remove particulate contamination from processed wafers. The cavitation sensor described herein may be integrated into the cleaning tank (batch process), single wafer cleaning tool, or even onto the wafer for online control and optimization of the cleaning process.

The cavitation sensor described herein may be used for ultrasonic cleaning of membranes, in particular delicate membranes for reverse osmosis, to control the amount of ultrasound energy to prevent rupture of the membrane. The cavitation sensor can clean surgical instruments in ultrasonic bathes. Since the cavitation sensor described herein has a simple design, it may be included in more expensive instruments.

The cavitation sensor described herein may be used in the research and design of flow systems where cavitation may occur, e.g. artificial heart-valves, high-power ultrasound systems for medical usage (shock wave lithotripsy, high intensity focused ultrasound), sonochemical reactors and ultrasound emulsifier.

Assuming a boundary layer with a linear velocity profile and a specific charge distribution it may be possible to determine the gradient of the velocity profile from the current signal. Thus, the cavitation sensor described herein may be able to measure wall shear stress and detect cavitation in liquids with high flow rates, e.g. to measure the flow in injection valves of car engines.

Figure 4:
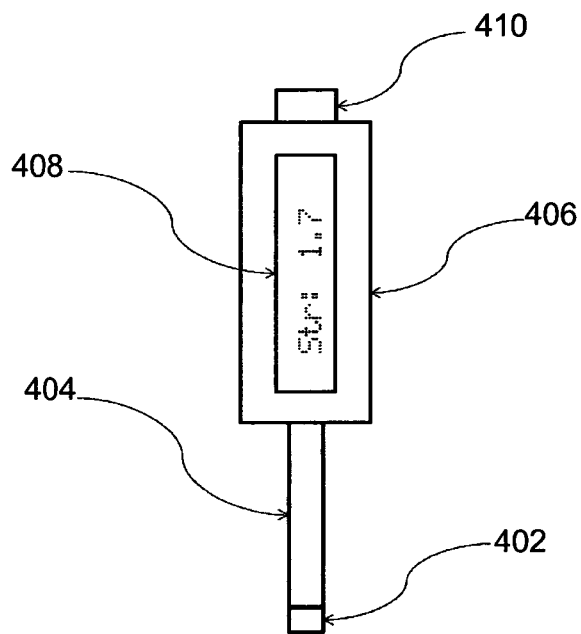
FIG. 4 shows a sketch of an ultrasonic cleaning monitor using a cavitation sensor as described herein.

FIG. 4 shows a sketch of an ultrasonic cleaning monitor 400 using a cavitation sensor 402.

Figure 6:
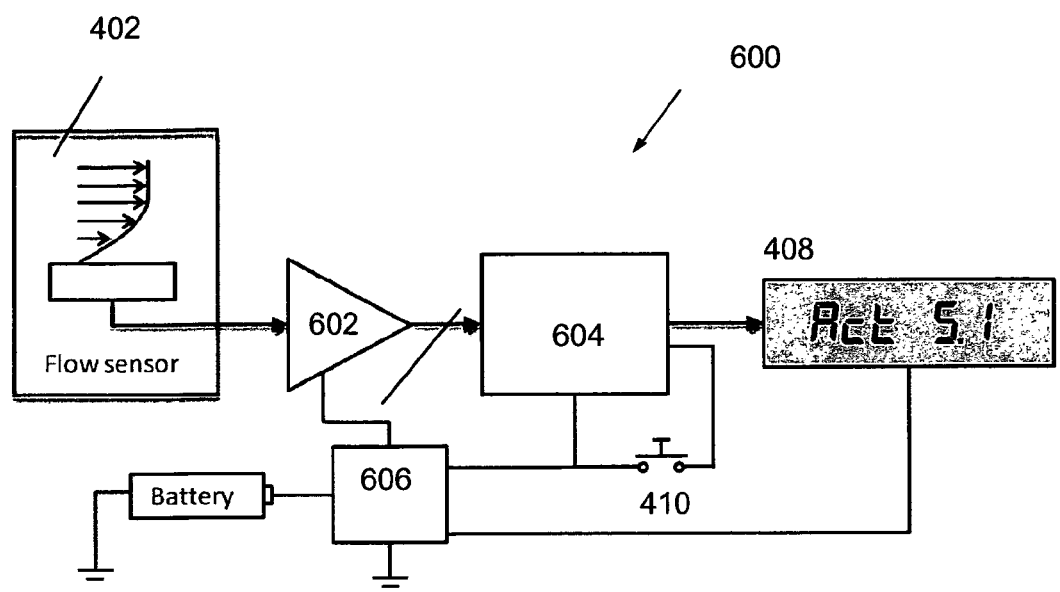
FIG. 6 shows an electronic board for the ultrasonic cleaning monitor of FIG. 4.

The cavitation sensor 402, which is adapted to be detachable and therefore replaceable, is mounted on a sensor holder 404 which is connected to a main body (not shown) holding an electronic board (see FIG. 6). The electronic board is within a waterproof housing 406, which gives access to a display 408. A button 410 on top of the housing 406 starts measurement. The electronic board analyzes the signal, e.g. the number of peaks per time interval, and the average strength of the peaks to characterize the cleaning strength of the ultrasonic cleaning bath.

The sensor holder 404 has to be long enough to reach all places within an ultrasonic cleaning bath. If an amplifier is inside the housing 406, the sensor holder 404 needs to be shielded against electromagnetic noise. However, the amplifier may also be placed at the bottom of the sensor holder 404 to increase the signal-to-noise ratio.

Figure 5:
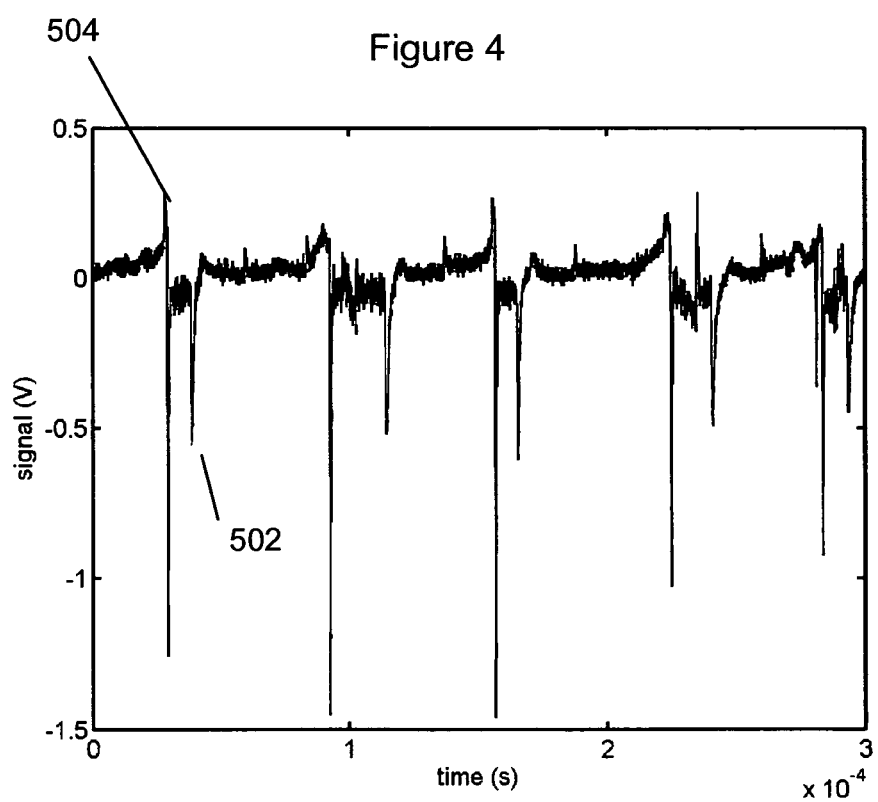
FIG. 5 shows a typical signal from a cavitation sensor as described herein.

FIG. 5 shows a typical signal from the sensor 402 in an ultrasonic cleaning bath which is amplified with a 200 MHz bandwidth transimpedance amplifier (current-voltage amplifier) and sampled at 1 GHz. The number and amplitude of peaks (negative 502 and positive 504) may be used to determine the quality of ultrasonic cleaning.

FIG. 6 shows an electronic board 600 for the ultrasonic cleaning monitor 400 (see FIG. 4). The electronic board 600 includes a signal conditioner 602 which amplifies the current signal from the cavitation sensor 402. An output voltage signal from the signal conditioner 602 is fed into a microcontroller 604 with a built in analog/digital (A/D) converter, power supply circuitry 606 and the display 408. The push button 410 is used to start the measurement. Instead of the microcontroller 604, a more sophisticated signal processor, capable of complex data analysis, e.g. Fourier transformation for analysis of the signal in the frequency space, may be used.

Typical ultrasonic cleaning baths operate between 20 kHz and 100 kHz. To capture the peaks shown in FIG. 5, the sampling rate should be at least 10 times higher than the bath's operation frequency. Thus, an 8 bit A/D converter, which is cheap and simple to configure, may be used for the microcontroller 604 to analyze the signal from the cavitation sensor 402.

Figure 7:
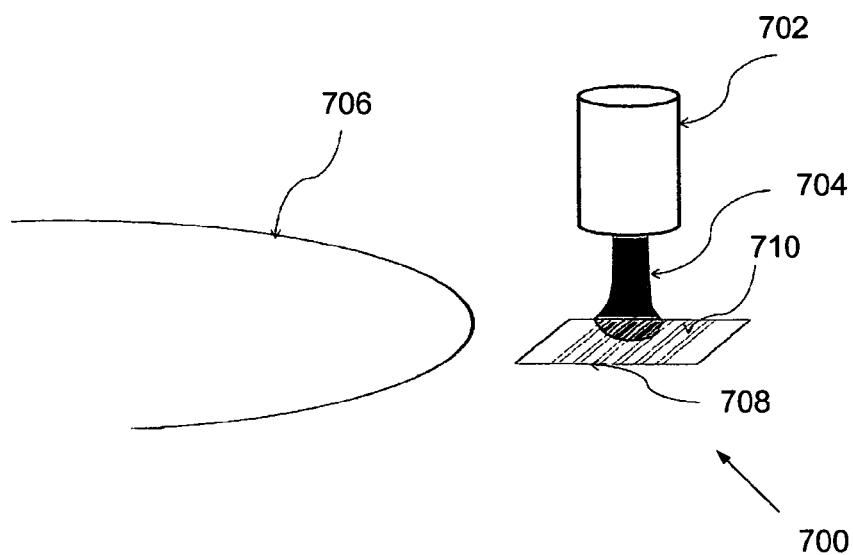
FIG. 7 shows a block diagram of a megasonic cleaning monitor, using a cavitation sensor as described herein, for a single wafer tool.

FIG. 7 shows a block diagram of a megasonic cleaning monitor, using a cavitation sensor 708, for a single wafer tool 700.

The single wafer-cleaning tool 700 uses a nozzle 702 in which ultrasonic pressure fluctuations in the megahertz frequency range are applied to a stream of water. The stream exits the nozzle 702 and a water jet 704 impinges on a wafer 706 and spreads on the surface. The water jet 704 also transmits ultrasonic vibrations to the wafer 706 surface.

The cavitation sensor 708 is placed on a calibration pad 710 next to the wafer 706. The nozzle 702 parameters (height of the water jet 704, flow rate, diameter of the water jet 704, and height of the wafer 706 surface) and the operation parameters of the megasonic transducer can be adjusted to for optimal cleaning.

The optimization procedure may be done before the wafer 706 is cleaned and possibly repeated during the cleaning process. Therefore, the sensor 708 is placed on a material with very similar acoustic properties as the wafer 706. The sensor pad 710 may consist of a single sensor, or multiple cavitations sensors to measure the spatial distribution of the cleaning. In one embodiment, around 10 sensors may be placed on the sensor pad 710, while the diameter of the jet may be around 3-5 mm.

Figure 8:
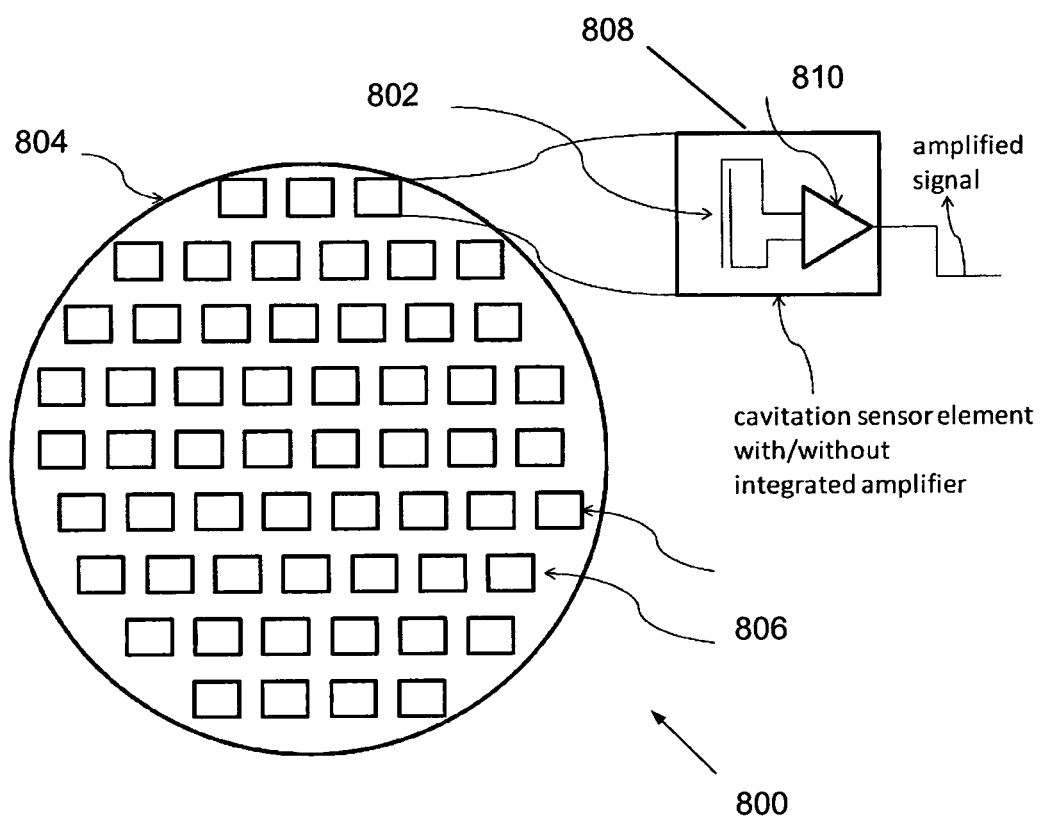
FIG. 8 shows a batch wafer tool using a plurality of cavitation sensors as described herein.

FIG. 8 shows a batch wafer tool 800 using a cavitation sensor 802.

In batch processing, multiple wafers are submerged into a megasonic cleaning bath. One of the slots 806 of a wafer holder 804 can hold a monitoring cleaning tool 808, so that the wafer holder 804 provides a multiple of cavitation sensors 802 placed on one or both surfaces. Each sensor 802 may be connected to an external transimpedance amplifier (not shown). It may also be possible to integrate an amplifier 810 onto the chip and the amplified signal is fed to an external processor (not shown) which analyzes the signal. To reduce the number of cable connections, multiplexing may be used. Therefore, a unique offset voltage may be added to each amplified sensor signal. This offset voltage needs to be higher than the typical signal level. A signal processor with sufficient sampling resolution can then identify the position through this offset voltage.

Experimental Data

Figure 9:
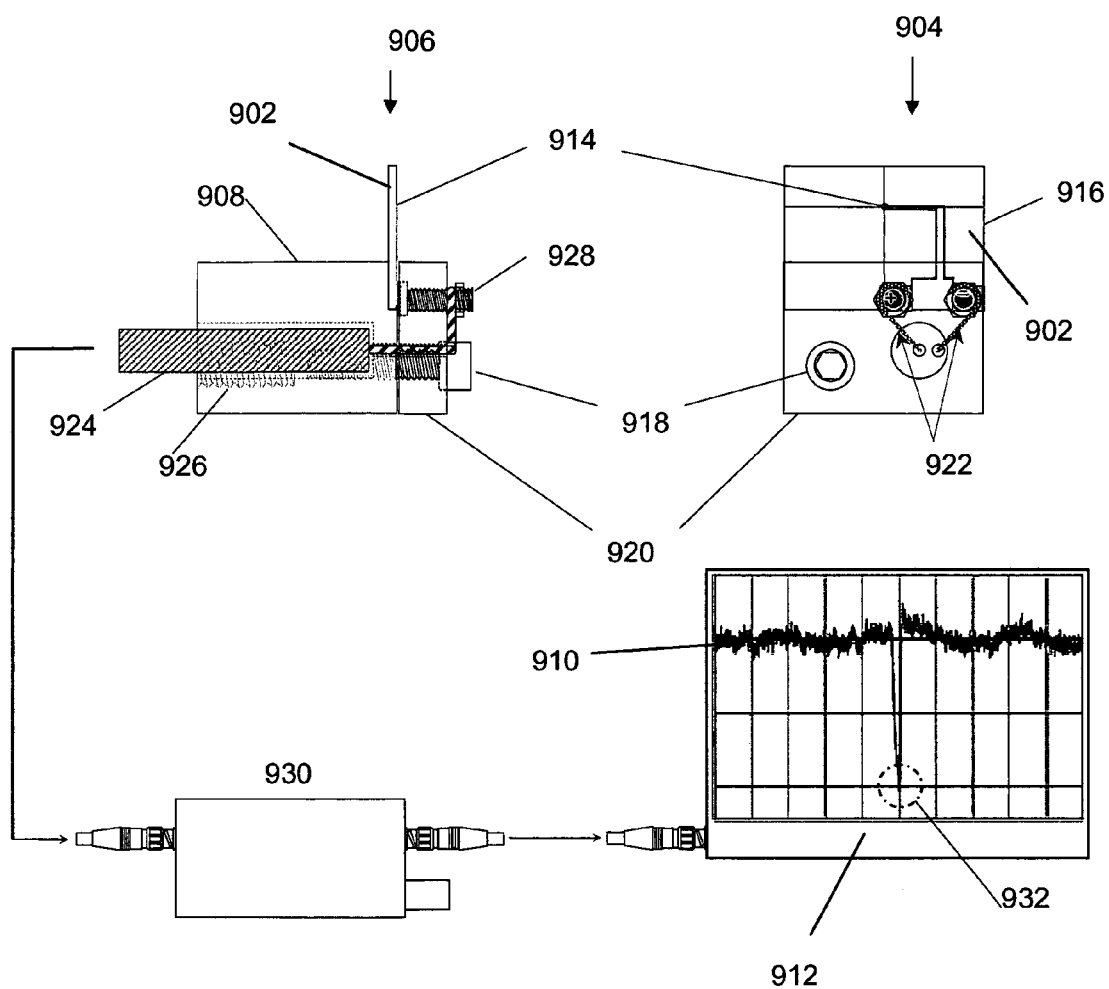
FIG. 9 shows a cavitation sensor being configured to measure cavitation.

FIG. 9 shows a cavitation sensor 902 being configured to measure cavitation. A front view 904 and a side view 906 are shown.

The cavitation sensor 902 is mounted in a traversable holder 908 and connected to a current amplifier (not shown). The signal 910 from the cavitation sensor 902 can be displayed using an oscilloscope 912.

The cavitation sensor 902 has a glass substrate 916 upon which is a sensing element 914. From both the front views 904 and 906, it can be seen that the cavitation sensor 902 is secured to the holder 908 through a M4 stainless steel hexagonal screw 918 running through a holder cover 920 to be received by a M6 thread 926 for attachment to the holder 908. Electrical contact to each of the terminals on the cavitation sensor 902 is through a pair of M3 stainless steel hexagonal screws 928. BNC positive and negative wires 922 run from the screws 928 to pass through the holder 908 to connect to a BNC cable 924. The BNC cable 924 is connected to a high speed current amplifier 930. The high speed current amplifier 930 is in turn connected to the oscilloscope 912. From the oscilloscope 912, detection of cavitation bubbles by the sensing element 914 is shown as a peak 932 in the signal 910.

Figure 10:
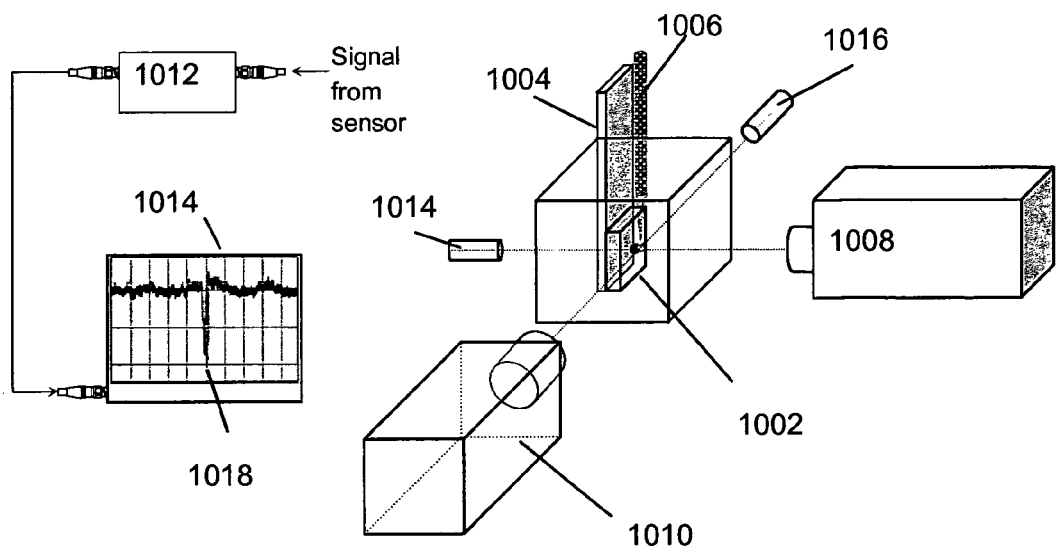
FIG. 10 shows a schematic of an experiment setup to test a cavitation sensor as described herein.

FIG. 10 shows a schematic of an experiment setup to test a cavitation sensor 1002.

In FIG. 10, the cavitation sensor 1002 is mounted on a sensor holder 1004. To correlate the sensor 1002 signal to bubble dynamics, a bubble induced by a pulsed laser beam 1006 is created in the vicinity of the cavitation sensor 1002. Simultaneous high speed video of the laser-induced bubble expanding and collapsing on top of the sensor 1002 is captured using high speed video cameras 1008 and 1010. Light sources 1014 and 1016 are used to illuminate the area where the bubbles were induced.

The sensor 1002 signal is sent to a current amplifier 1012 and recorded in a LeCroy oscilloscope 1014. Both the recorded signal and the high speed video are compared to evaluate the moment at which a signal 1018 is produced from the cavitation sensor 1002.

Figure 11:
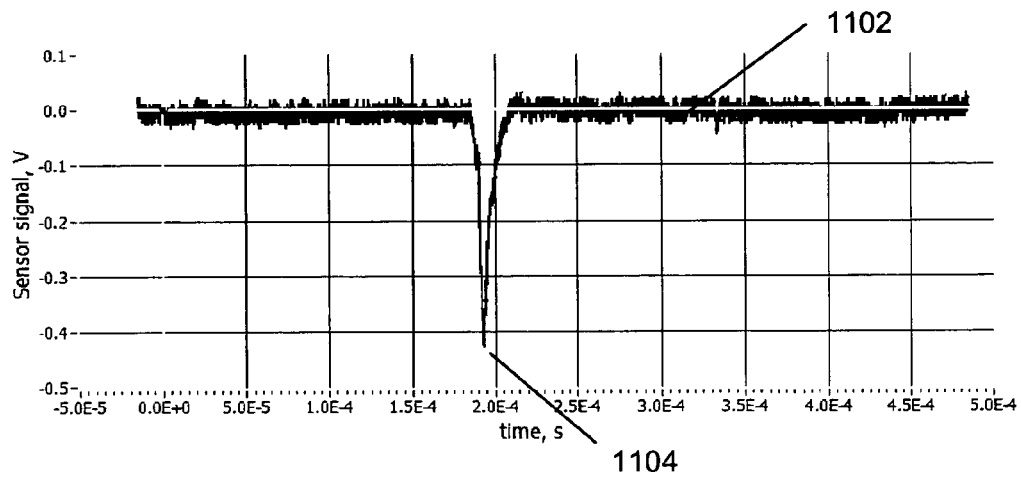
FIG. 11 shows a sensor signal trace from the cavitation sensor of FIG. 10.

FIG. 11 shows a sensor signal trace 1102 from the cavitation sensor 1002 (see FIG. 10). The sensor signal trace 1102 has a negative peak 1104 at around t=193.57 μs, corresponding to the moment the bubble impacted onto the sensor 1002 negative electrode and expanded to the positive electrode. The measured potential of the signal produced by the bubble is around −0.43 V. Before and after the bubble impacted onto the surface, the measured potential signal value is around 0V.

Figure 12:
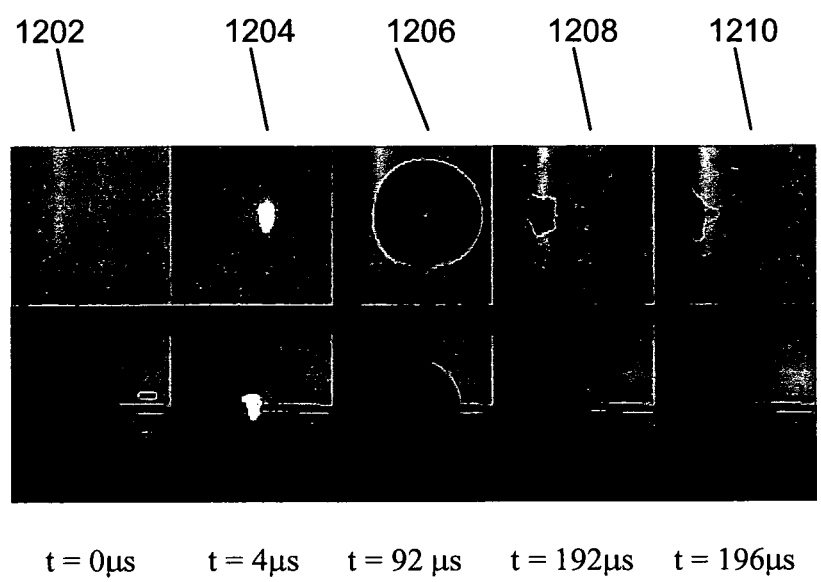
FIG. 12 shows still images from a high speed video capture taken during the experiment setup of FIG. 10.

FIG. 12 shows still images from the high speed video capture taken by the camera 1010 (see FIG. 11) and the camera 1008 (see FIG. 11). The still images shown depict before the laser-induced bubble is created (see column 1202) to after the laser-induced bubble impacted (see column 1210) the sensing element 1206. The top row in FIG. 12 shows images taken from the camera 1010, i.e. a side view, while the bottom row shows images taken from the camera 1008, i.e. a top view. The dotted white line denotes the position of the boundary where the sensor is located. The images in each of the columns 1202 to 1210 refer to a same time interval.

The images, in the first column 1202, show the moment before the bubble is created. The bottom image shows the electrodes geometry of the cavitation sensor.

The second column 1204 shows after a bubble is created. The bubble reached its maximum volume in the third column 1206, after which the bubble started to contract. The bubble reached its minimum volume in the fourth column 1208 at t=192 µs and during its re-expansion, the bubble boundary moved from a negative to a positive electrode, at t=196 µs, as seen in columns 1208 and 1210 respectively. The video was captured at a frame rate of 250,000 frames per second and an exposure time of 1 µs. Since the oscilloscope 1014 (see FIG. 10) sampling rate is faster than the cameras 1010 and 1018 frame rate, the moment at which the peak 1104 (see FIG. 11) is produced occurs between t=192 µs and t=196 µs after the bubble is created. The advantage of laser-induced bubbles is that virtually identical bubbles can be produced; allowing repeated assessing of the sensor signal trace 1102 (see FIG. 11). In a second test performed with a bubble of the same size and separated the same distance from the sensor, a peak with a potential value of −0.48V occurring at t=193.48 µs was detected.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A cavitation sensor for detecting bubbles in a liquid, the cavitation sensor comprising:
    a substrate having an insulative surface; and
    an electrode arrangement provided on or within the insulative surface of the substrate; wherein the electrode arrangement comprises a first electrode and a second electrode being isolated from each other by the insulative surface, each of the first and the second electrode comprising a sensing portion, wherein a spacing between the sensing portion of the first electrode and the sensing portion of the second electrode is adapted to allow charge flow between the first electrode and the second electrode caused by cavitation occurring at the sensing portion;
    wherein the sensing portion of the first electrode and the sensing portion of the second electrode are configured to remain stationary relative to the substrate, to detect a change in a velocity of liquid flowing parallel to the substrate surface where the electrode arrangement is provided on.

2. The cavitation sensor of claim 1, wherein the electrode arrangement is a layer having a thickness of around 300 nm.

3. The cavitation sensor of claim 1, wherein the sensing portion of the first electrode and the sensing portion of the second electrode each comprise a strip.

4. The cavitation sensor of claim 3, wherein the strip of the first electrode has an end which is disc shaped, while the strip of the second electrode has an end that partially surrounds the disc shaped end of the first electrode to form a crook shape.

5. The cavitation sensor of claim 3, further comprising a tapered portion formed by the spacing between the strip of the first electrode and the strip of the second electrode tapering towards the corresponding end of the first electrode and the second electrode.

6. The cavitation sensor of claim 3, wherein the strip of the first electrode is parallel to the strip of the second electrode.

7. The cavitation sensor of claim 6, wherein the ratio of the space between the strip of the first electrode and the strip of the second electrode; and the width of the strip of the first electrode and the strip of the second electrode is any one of the values of 1, 1.5, 1.75 and 2.

8. The cavitation sensor of claim 1, wherein the electrode arrangement comprises one or more arrays, each array comprising one or more pairs of first electrodes and second electrodes.

9. The cavitation sensor of claim 8, wherein each array comprises
    a first common terminal to which each of the first electrodes of the one or more pairs are coupled; and
    a second common terminal to which each of the second electrodes of the one or more pairs are coupled.

10. The cavitation sensor of claim 9, wherein the pairs of electrodes are arranged such that first electrodes and second electrodes alternate with each other.

11. The cavitation sensor of claim 10,
    wherein the first common terminal and the second common terminal are arranged parallel to each other,
    wherein the first and second electrodes are arranged parallel to each other, and
    wherein the first and second electrodes are arranged perpendicular to the first common terminal and the second common terminal.

12. The cavitation sensor of claim 9, wherein the first common terminals of a first array of the one or more arrays and a second array of the one or more arrays are coupled together, or wherein the second common terminals of the first array and the second array are coupled together.

13. The cavitation sensor of claim 8, wherein the distance between adjacent electrodes for one of the one or more arrays is different from the distance between adjacent electrodes for another of the one or more arrays.

14. The cavitation sensor of claim 8, wherein the distance between adjacent electrodes in all of the one or more arrays is the same.

15. The cavitation sensor of claim 8, wherein the maximum distance between adjacent electrodes for the one or more arrays is about less than half of the diameter of the bubble to be detected.

16. The cavitation sensor of claim 1, wherein the spacing between the sensing portion of the first electrode and the sensing portion of the second electrode is smaller than a diameter of a bubble to be detected.

17. The cavitation sensor of claim 1, wherein the maximum spacing between the sensing portion of the first electrode and the sensing portion of the second electrode is about less than half of the diameter of the bubble to be detected.

18. The cavitation sensor of claim 1, wherein the sensing portion of the first electrode and the sensing portion of the second electrode are provided on a common plane.

19. The cavitation sensor of claim 1, wherein the sensing portion of the electrode arrangement is provided on the insulative surface of the substrate, while at least a portion of the remainder of the electrode arrangement is provided within the insulative surface of the substrate.

20. The cavitation sensor of claim 1, wherein the substrate is entirely made of an insulative material.

* * * * *